(12) United States Patent
Plante et al.

(10) Patent No.: US 8,128,826 B2
(45) Date of Patent: *Mar. 6, 2012

(54) ETHANOL PROCESSING WITH VAPOUR SEPARATION MEMBRANES

(75) Inventors: Pierre Plante, St-Romuald (CA); Bruno de Caumia, Stoneham (CA); Christian Roy, Quebec (CA); Gaétan Noël, St-Hubert (CA)

(73) Assignee: Parker Filtration BV, Arnhem (NL)

( * ) Notice: Subject to any disclaimer, the term of this patent is extended or adjusted under 35 U.S.C. 154(b) by 953 days.

This patent is subject to a terminal disclaimer.

(21) Appl. No.: 12/038,284

(22) Filed: Feb. 27, 2008

(65) Prior Publication Data

US 2008/0207959 A1 Aug. 28, 2008

Related U.S. Application Data

(60) Provisional application No. 60/892,098, filed on Feb. 28, 2007, provisional application No. 60/892,087, filed on Feb. 28, 2007.

(30) Foreign Application Priority Data

Mar. 9, 2007 (CA) .................................... 2581761

(51) Int. Cl.
  B01D 61/36 (2006.01)
  B01D 3/36 (2006.01)
  B01D 3/00 (2006.01)
(52) U.S. Cl. .................. 210/640; 95/45; 95/52; 203/18; 203/19; 203/27; 203/25; 203/DIG. 8; 435/161; 435/295.3; 435/297.1

(58) Field of Classification Search .................... None
See application file for complete search history.

(56) References Cited

U.S. PATENT DOCUMENTS

| 4,217,178 | A | | 8/1980 | Katzen et al. |
| 4,236,036 | A | | 11/1980 | Dixon et al. |
| 4,345,973 | A | | 8/1982 | Ladisch et al. |
| 4,407,662 | A | | 10/1983 | Ginder |
| 4,444,571 | A | * | 4/1984 | Matson .............................. 95/48 |
| 4,541,897 | A | | 9/1985 | Sommer et al. |

(Continued)

FOREIGN PATENT DOCUMENTS

WO  2005007277 A1  1/2005

OTHER PUBLICATIONS

Richard W. Baker, "Future Directions of Membrane Gas Separation Technology", Ind. Eng. Chem. Res. 2002, 41, 1393-1411.

(Continued)

*Primary Examiner* — Krishnan S Menon
(74) *Attorney, Agent, or Firm* — Bereskin & Parr LLP/S.E.N.C.R.L., s.r.l.

(57) ABSTRACT

A process for separating vapors, for example for separating water from ethanol, uses a gas separation membrane unit. Permeate from the membrane unit is compressed and may be used for example as heating steam for distillation. The membrane unit may have two or more stages. Permeate from a stage may be condensed and used for example as fermentation make up water, compressed and fed to the permeate from an upstream stage or heating steam, or fed to another membrane stage for further dewatering. The gas separation membrane unit may be used to remove water from a fermentation broth that has been partially dewatered, for example by one or more of a distillation column or molecular sieve.

13 Claims, 8 Drawing Sheets

U.S. PATENT DOCUMENTS

| | | | |
|---|---|---|---|
| 4,978,430 | A | 12/1990 | Nakagawa et al. |
| 5,013,447 | A | 5/1991 | Lee et al. |
| 5,030,775 | A | 7/1991 | Sircar |
| 5,147,550 | A * | 9/1992 | Wijmans et al. ............... 210/640 |
| 5,160,046 | A | 11/1992 | Pasternak |
| 5,294,304 | A | 3/1994 | Kario et al. |
| 5,585,527 | A | 12/1996 | Marker |
| 5,616,247 | A * | 4/1997 | Mita et al. ..................... 210/640 |
| 5,681,433 | A | 10/1997 | Friesen et al. |
| 5,723,639 | A | 3/1998 | Datta et al. |
| 6,375,803 | B1 | 4/2002 | Razzaghi et al. |
| 6,755,975 | B2 | 6/2004 | Vane et al. |
| 7,556,677 | B2 | 7/2009 | Cranford et al. |
| 2006/0070867 | A1 * | 4/2006 | Ikeda ............................. 203/25 |
| 2006/0117955 | A1 | 6/2006 | Cranford et al. |
| 2007/0000769 | A1 | 1/2007 | Brown |
| 2007/0031954 | A1 | 2/2007 | Mairal et al. |
| 2008/0207959 | A1 | 8/2008 | Plante et al. |

OTHER PUBLICATIONS

Andreas Peschel et al., "A super Structure Optimization Approach for the Design of Corn-Based Ethanol Plants", Paper 648e, Session: Sustainable Engineering in Process Development, AICHE Annual Meeting, San Francisco, Nov. 12-17, 2006.

Seungdo Kim et al., "Environmental aspects of ethanol derived from no-tilled corn grain: nonrenewable energy consumption and greehouse gas emissions", Biomass and Bioenergy 28 (2005) 475-489.

* cited by examiner

ETHANOL PROCESSING WITH VAPOUR SEPARATION MEMBRANES

This application claims the benefit under 35 USC 119(e) of U.S. patent application Ser. Nos. 60/892,087 filed on Feb. 28, 2007 and 60/892,098 filed on Feb. 28, 2007, both of which are incorporated herein in their entirety by this reference to them.

FIELD

This specification relates to alcohol processing or gas or vapour separation.

BACKGROUND

The following is not an admission that anything discussed below is citable as prior art or part of the common general knowledge.

Plant matter, for example carbohydrates or cellulose, may be fermented to produce a liquid, sometimes called beer, that is primarily water but includes ethanol. Dewatering this beer may produce ethanol that is substantially free of water, for example having less than about 1% water by volume, which may be used as a fuel or a fuel additive suitable for use in, for example, internal combustion automobile engines. Distillation can be used to partially dewater the beer, but the energy required in the distillation column reflux loop per volume percent of water removed increases as the ethanol content increases for a given number of trays in the column. At about 97% ethanol by volume, the ethanol/water azeotrope has been reached and simple distillation is no longer effective. Other techniques, such as azeotropic distillation or molecular sieves may then be used. The energy requirement of these processes is a significant problem as is the amount of water required for fermentation. Solids produced in the fermentation process, sometimes called stillage, may be useful for animal feed but must be dewatered. Dewatering involves a first step in which the stillage is dewatered typically to about a 70% moisture content measured on a dry basis and a second step in which the stillage is dried further to about a 15% moisture content measured on a dry basis as required for sale as distillers dried grains and solubles, which requires a significant amount of energy.

U.S. Pat. No. 4,978,430 describes a process in which an evaporation vessel produces a mixture of an organic compound vapour and water vapour. The mixture permeates through an aromatic polyimide gas separation membrane. The permeated vapour has an increased concentration of water vapour and a product vapour has a reduced concentration of water vapour. The permeated vapour passes through a condenser and is then returned to the evaporation vessel.

International Patent Application No. PCT/CA004/001047 filed on Jul. 16, 2004 describes an asymmetric integrally skinned membrane. The membrane can have a vapour permeance to water at least $1 \times 10^{-7}$ mol/m$^2$sPa at a temperature of about 30° C. to about 200° C. The membrane may have a vapour permeance selectivity of at least 50, preferably at least 250 for water/ethanol at a temperature of about 140° C. Application No. PCT/CA2004/001047 is incorporated herein in its entirety by this reference to it.

INTRODUCTION

The following introduction is not intended to limit or define any claim. One or more inventions may reside in any combination of one or more process steps or apparatus elements drawn from a set of all process steps and apparatus elements described below or in other parts of this document, for example the detailed description, claims or figures.

This specification describes a process for removing water from an aqueous alcohol mixture, for example ethanol, using a heat driven process, for example distillation, and a gas separation membrane unit. A permeate is produced from the membrane unit that is substantially water vapour or ethanol free. This water vapour is compressed and used to transfer heat to one or more other parts of the process, for example distillation, drying stillage, heating beer or pre-heating vapours before membrane separation. The water vapour may be condensed and used in the process, for example as make up water for fermentation. Heat energy in a product vapour may also be used, for example to dry stillage or pre-heat the beer before distillation.

This specification also describes processes for dewatering an ethanol feed using a plurality of gas separation membrane stages, for example two, three or more. The stages may be arranged in series in relation to a feed/retentate/product flow. Permeate from an upstream stage may be compressed and used to heat another process step. Permeate from a downstream stage may be condensed for use as make up water, or compressed and added to an upstream permeate stream. A permeate stream may be fed through another membrane stage for further dewatering before being used to transfer heat. One or more of the possibilities described above may be combined.

A membrane unit may also be used to process a partially dehydrated stream within a plant. For example, a combined process having a gas separation membrane unit and a molecular sieve unit is described.

DETAILED DESCRIPTION

Various apparatuses or processes will be described below to provide an example of an embodiment of each claimed invention. No embodiment described below limits any claimed invention and any claimed invention may cover processes or apparatuses that are not described below. The claimed inventions are not limited to apparatuses or processes having all of the features of any one apparatus or process described below or to features common to multiple or all of the apparatuses described below. It is possible that an apparatus or process described below is not an embodiment of any claimed invention. The applicants, inventors and owners reserve all rights in any invention disclosed in an apparatus or process described below that is not claimed in this document and do not abandon, disclaim or dedicate to the public any such invention by its disclosure in this document.

Figure 1:
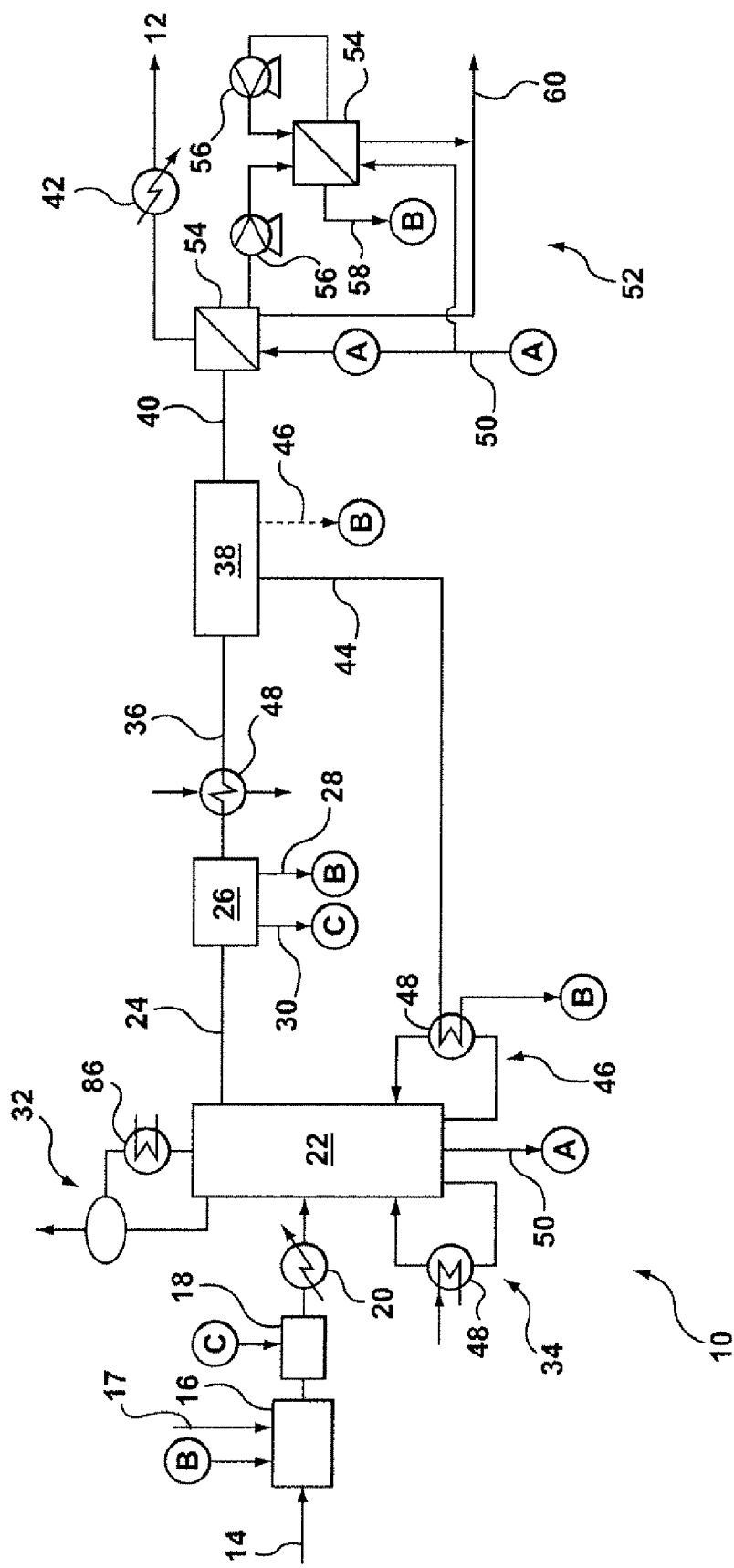
FIG. 1 is a simplified schematic flow sheet of an ethanol processing plant.

FIG. 1 shows a plant 10 used to produce a product 12. The product 12 may be used as fuel grade ethanol or may have about 99% or greater ethanol by volume. The raw feed 14 to the plant 10 is a plant material that may be fermented to produce ethanol, for example carbohydrates or cellulose, for example from corn kernels, sugarcane or switchgrass. The raw feed 14 passes to a fermenter 16 which is also fed with water 17 as well as yeast and other fermentation inputs. The fermenter 16 outputs a beer which may be temporarily stored in a beer tank 18. The beer contains ethanol but is mostly water. The beer may contain about 3 to 15 percent, or about 10 to 12 percent, ethanol by volume, although up to 20 percent by volume or more may be possible. The beer then flows, optionally passing through a beer pre-heater 20, to a distillation column 22. The distillation column 22 may be a single, multi-stage or multi-effect column or columns for producing a distilled ethanol 24 with an increased ethanol content. For example, the distillation column 22 may be or comprise a stripping column or zone or a beer column or zone and increase the ethanol content to at least 45% by volume but typically less than 75% by volume. Alternately, the distillation column 22 may further comprise a rectification column or zone and increase the ethanol content to 75% by volume or more, more typically 90% or more up to a value approaching 97% by volume. Although aspects of the invention may be useful when the beer is distilled to an ethanol content of 75% by volume or more, energy consumption for the plant 10 as a whole is likely to be less when the beer is distilled to 75% ethanol by volume or less which may be done in a single column. The distillation column 22 may have a reflux loop 32 and a reboiler loop 34.

The distilled ethanol 24, as a vapour, passes through a scrubber 26. Scrubber 26 will be described further below but removes particles and any liquid droplets from the distilled ethanol 24. The particles are contained in a first liquid 28 which may be returned to the fermenter 16 as make up cook water and a second liquid 30 which may be returned to the beer tank 18.

Scrubbed ethanol 36 leaves the scrubber 26 and flows to the membrane unit 38. The membrane unit 38 will be described in further detail below. In general, the membrane unit 38 produces a product vapour 40 that is nearly water free, for example having 99% or more ethanol by volume. The membrane unit 38 also produces compressed vapour permeate 44 and, optionally, condensed permeate 46. Both permeates 44, 46 have only trace ethanol contents, for example 2% ethanol by volume or less. Condensed permeate 46, if any, may be returned to the fermenter 16 as make up cook water, or optionally sent to the distillation column 22. For reasons that will be discussed further below, compressed vapour permeate 44 carries heat energy and may be used to heat another part of the process. In FIG. 1, for example, the compressed vapour permeate 44 is used in a second reboiler loop 46 to heat the liquids in the bottom of distillation column 22. Optionally, condensed vapour permeate 44 may be used to replace or further supply heat to reboiler loop 34, beer preheater 20, a stillage dehydrator, a heater 48 or other apparatuses or processes. After transferring its heat energy, compressed vapour permeate 44 may become a liquid, primarily water, and be re-used, for example as make up cook water for fermenter 16.

Stillage 50 may be withdrawn from distillation column 22 or optionally from the beer feed to distillation column 22. Stillage 50 may be partially dewatered by mechanical means and then sent through a drying circuit 52. In drying circuit 52, stillage passes through one or more heat exchangers 54. Heat exchangers 54 use heat from product vapour 40 and suction from pumps 56 to encourage water to evaporate from stillage 50. Pumps 56 also transport the evaporated water until it condenses into reclaimed stillage water 58 which may be used, for example, in fermenter 16. Dewatered stillage 60 may be, for example, about 30 percent solids by weight or more.

Figure 2:
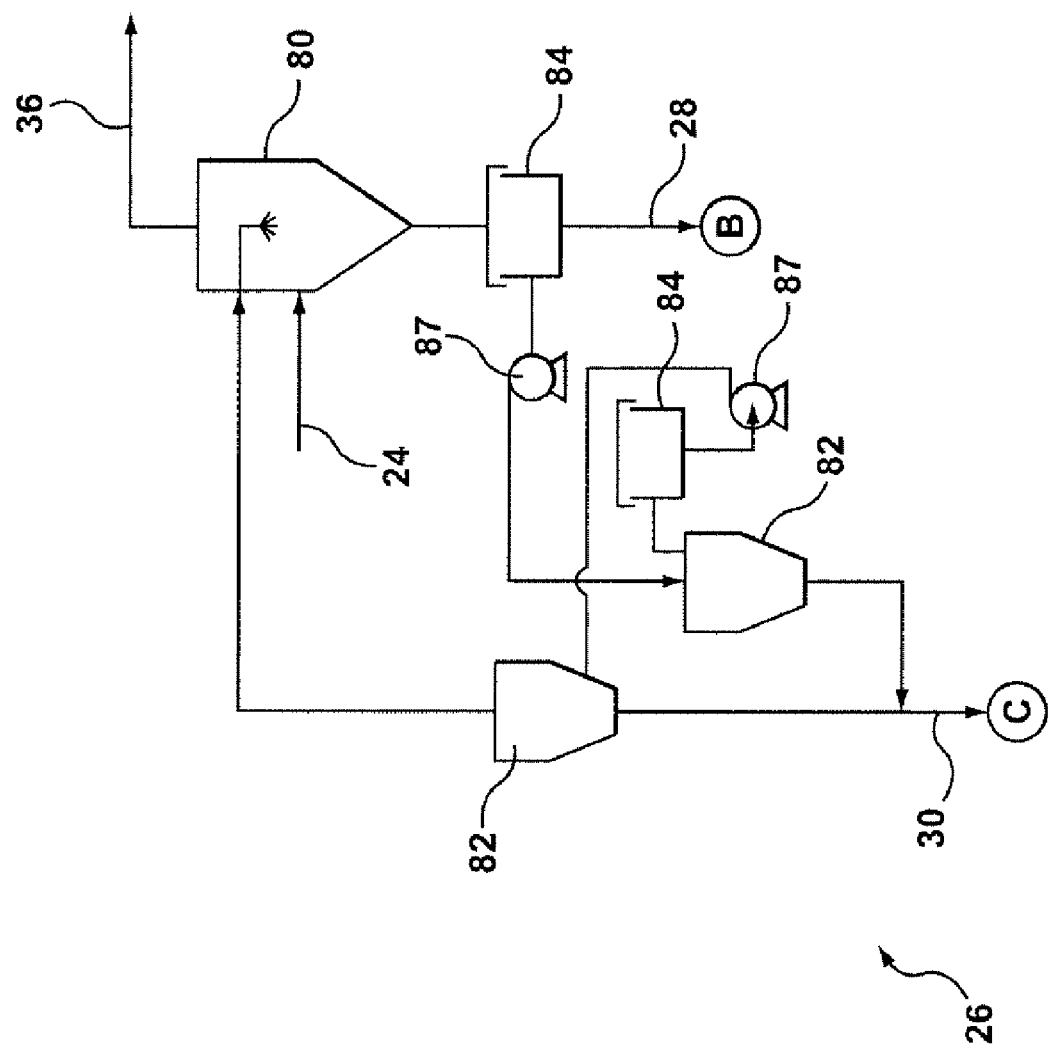
FIG. 2 is a simplified schematic flow sheet of a scrubber of the plant of FIG. 1.

FIG. 2 shows scrubber 26 in greater detail. Scrubber 26 has a spray tank 80, tank 84, pumps 87, and forward cleaners 82 configured and connected as shown. Scrubber 26 removes particles and liquid droplets, if any, from the vapours by entraining the particles and droplets in water.

Various alternate membrane units 38 will be described below with reference to FIGS. 3 to 6. Each of FIGS. 3 to 6 show a different example of a membrane unit 38. Other examples of membrane units 38 may be created by combining all or parts of one or more of the examples of FIGS. 3 to 6. The membrane units 38 have multiple membrane stages 80. Each membrane stage 80 may be a membrane module, a stage in an internally staged module, or a set of modules or internal stages in parallel. Membrane modules may use polymeric membranes, for example of polyimide hollow fibers. A hollow fibre module may be fed to the insides of the hollow fibres. The membranes may be asymmetric integrally skinned polyimide membranes as described, for example, in International Patent Application No. PCT/CA2004/001047. Such membranes can have a vapour permeance for water of $4\times10^{-7}$ mol/m$^2$sPa or more at about 80° C. The membranes can have a vapour permeance selectivity of 250 or more for water/ethanol at about 140° C. The membrane unit 38 may also be equipped with a vapour compressor 82. The vapour compressor 82 compresses permeate vapours adiabatically which causes them to rise in temperature. The increased temperature allows the heat energy in the permeate vapours to flow to, and heat, lower temperature vapours, gases or liquids. The heat energy in the permeate vapours (sensible heat plus latent heat of condensation) can then be used for heating purposes in other parts of the process. The vapour compressor 82 may be, for example, a radial type fan or compressor that provides a compression ratio of less than 1:40, for example, between 1:2 and 1:10. Although the vapour compressor 82 requires energy to turn the compressor, at relatively low compression ratio the temperature rise of the vapours permits their use as a heat source, for example in a re-boiler.

Figure 3:
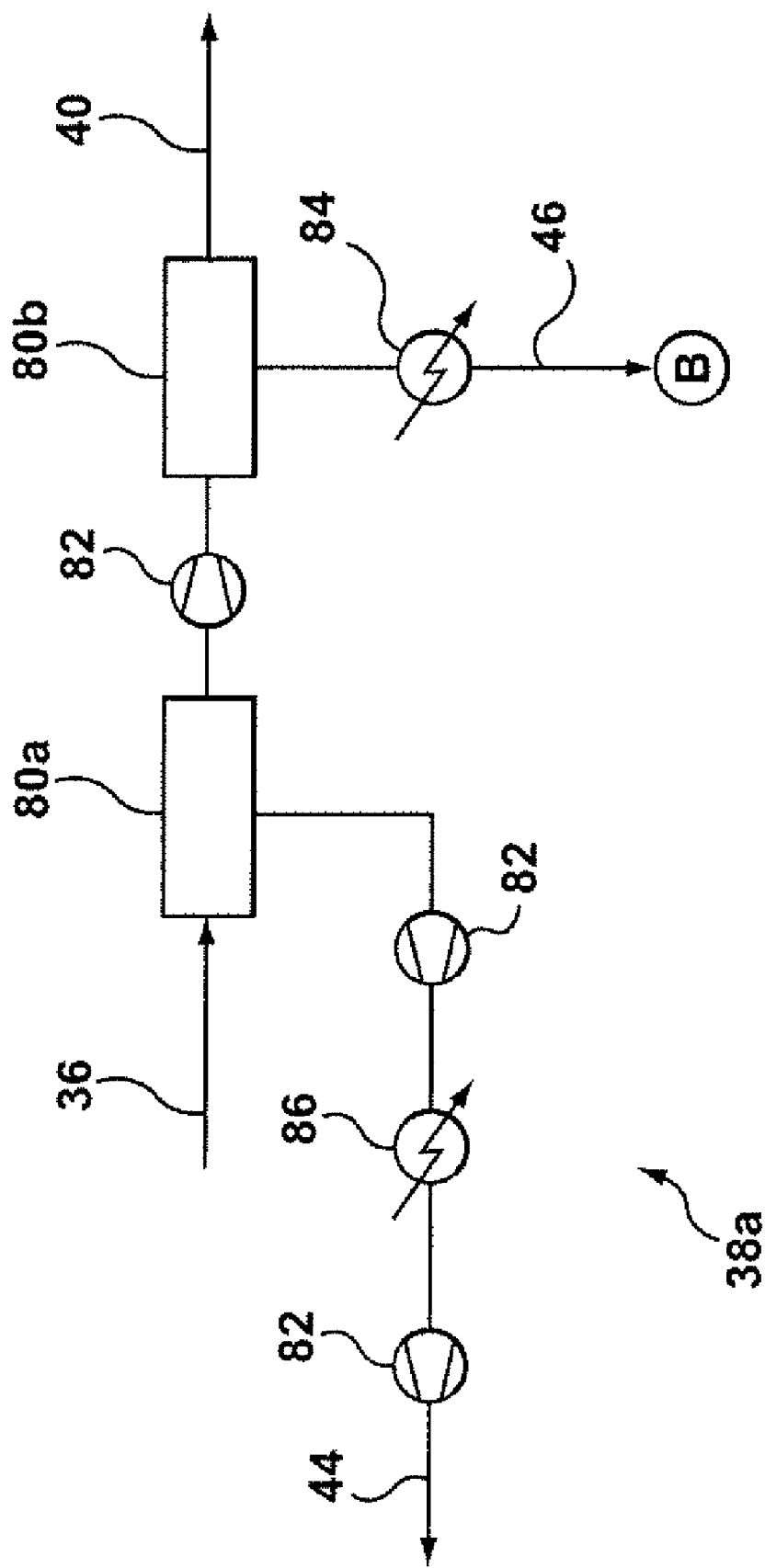
FIGS. 3 to 6 are simplified schematic flow sheets of alternate membrane units of the plant of FIG. 1.

FIG. 3 shows a two stage membrane unit 38a. Permeate from a first stage 80a is sent to a vapour compressor 82 and used as heating steam for distillation column 22 as described above. Retentate from the first stage 80a becomes feed for a second stage 80b. Permeate from second stage 80b passes through a condenser 84 before being reused as cook water for fermentation as described above. The use of a compressor 82 to increase the retentate pressure from first stage 80a is an option, or to compress permeate from the first stage 80a before it reaches a cooler 86.

Figure 4:
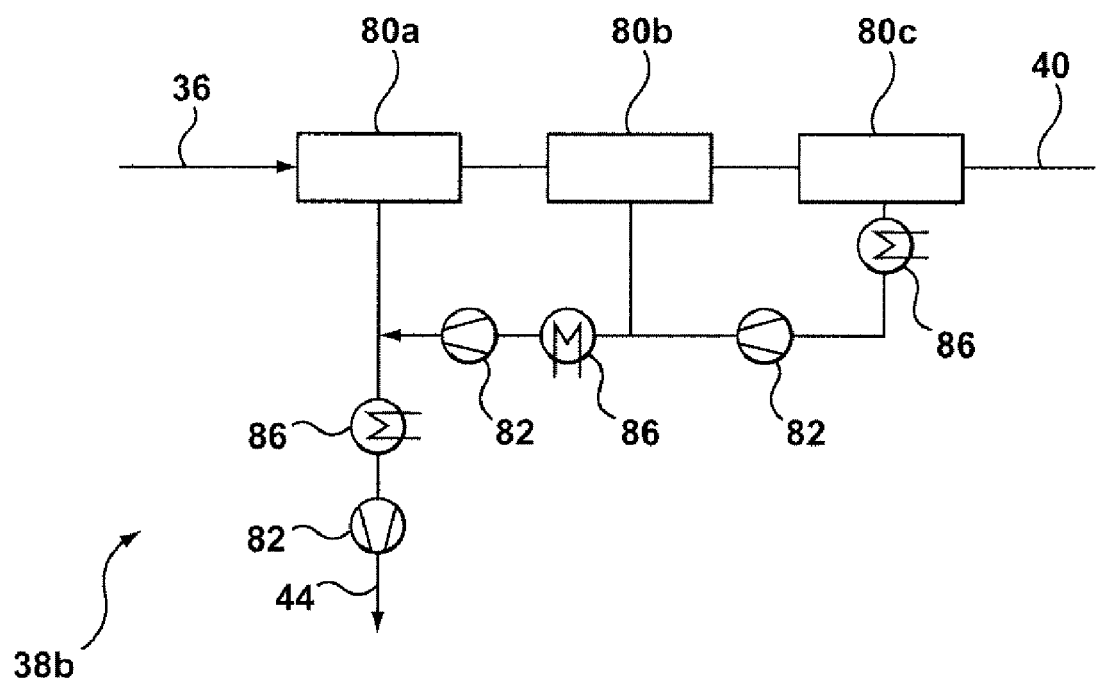

FIG. 4 shows a second membrane unit 38b having three stages 80a, 80b and 80c. Permeate from these stages 80a, 80b, 80c may have a temperature of about 100° C., but declining downstream, and pressures of about 30-60 kPa (absolute), 5-15 kPa (absolute) and 1.5 to 4 kPa (absolute) respectively. Optionally, the third stage 80c and its permeate flow may be omitted to create a two stage membrane unit. For each downstream unit 80b, 80c, the permeate is collected and passed through a cooler 86 and a vapour compressor 82 before joining the permeate from an adjacent upstream stage 80b upstream of its vapour compressor 82. Cooler 86 may assist in creating a permeate side vacuum to withdraw permeate and also allows the permeate vapour to be compressed to a higher pressure while contributing to reducing the outlet temperature of the compressed permeate. By recompressing permeate, and recycling it as heating steam, the second membrane unit 38b maximizes energy recovery. Compressed vapour permeate may have a temperature of 150° C. or more and a pressure of 200 kPa (absolute) or more.

Figure 5:
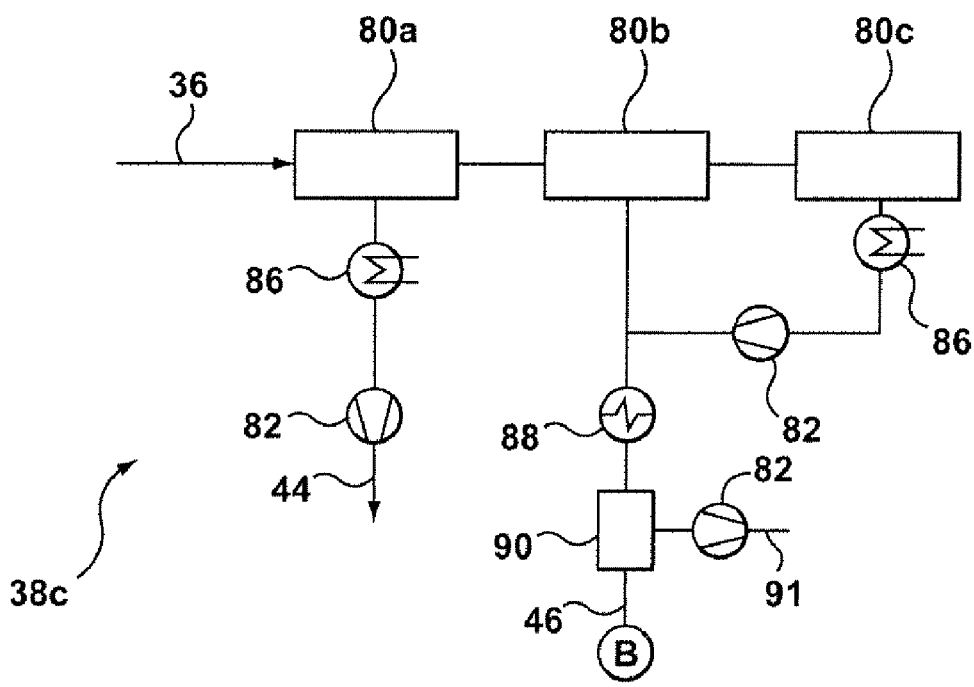

FIG. 5 shows a third membrane unit 38c. The third membrane unit 38c combines aspects of the first membrane unit 38a and second membrane unit 38b. Two permeate streams 44, 46 are produced, but the condensed permeate 46 is produced from two downstream stages 80b, 80c connected with recycle and compression of the further downstream permeate to the adjacent upstream permeate as in the first membrane unit 38a. The combined permeate of downstream stages 80b, 80c passes through a condenser 88, and a holding tank 90 and is then recycled to the fermenter 16. The configuration of membrane unit 38c provides balanced cost and energy improvements. A compressor 82 connects the holding tank 90 to an outlet 91 to atmosphere.

Figure 6:
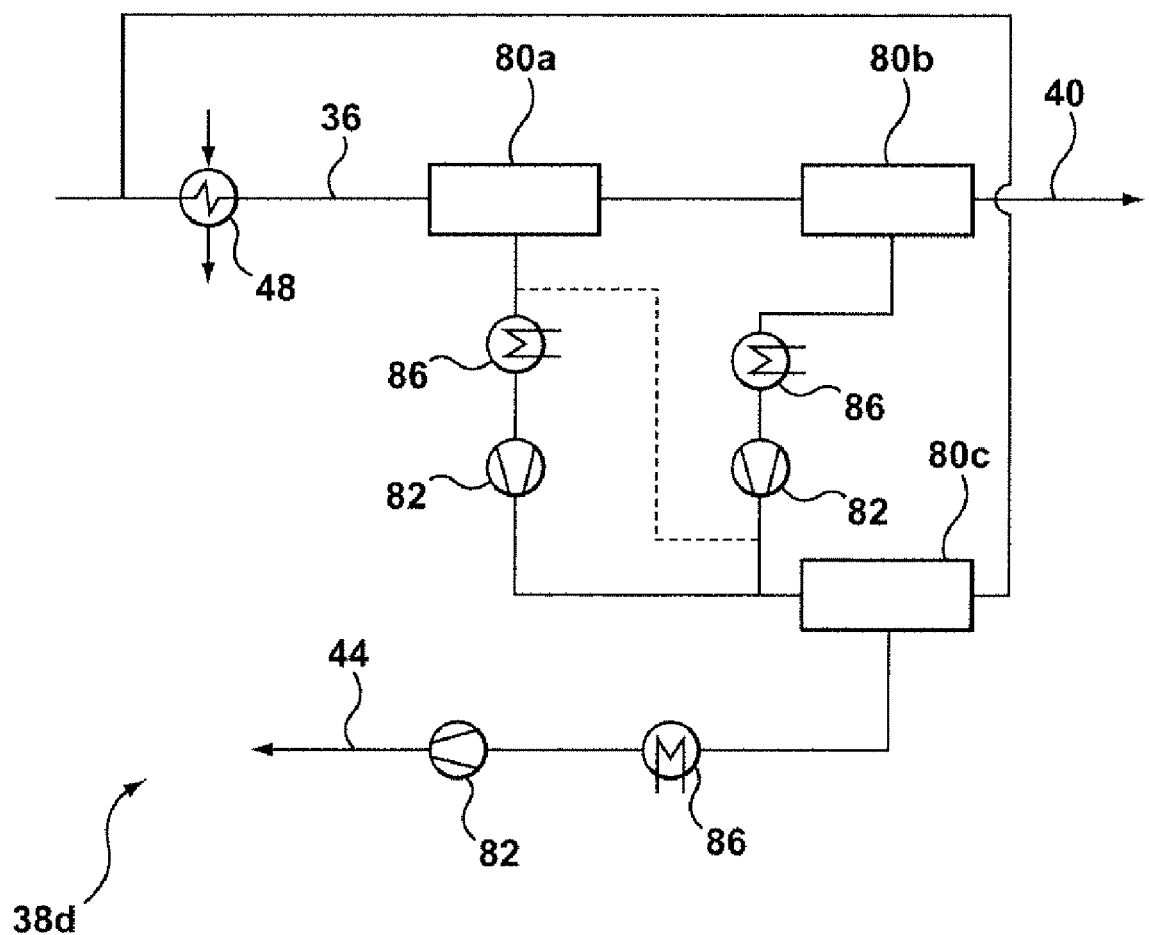

FIG. 6 shows a fourth membrane unit 38d. Permeate from first and second stages 80a, 80b is compressed and fed to third stage 80c individually as shown in the solid line or by joining the further downstream permeate to the adjacent upstream permeate before its compressor 82 as shown with the dashed line. Permeate from the third stage 80c is recycled upstream of the heater 48 upstream of the first stage 80a. Permeate vapour from the third stage is compressed and recycled as has been discussed above. In the third membrane unit 38d, the permeate is re-separated which increases ethanol recovery over the previous membrane units 38a, b, c. Compressed vapour permeate 44 may be 0.1% ethanol by volume or less, or essentially steam. Similarly, the permeate from any one or more stages described in FIGS. 3 to 5 may be further separated as shown in FIG. 6 to improve ethanol recovery.

Figure 7:
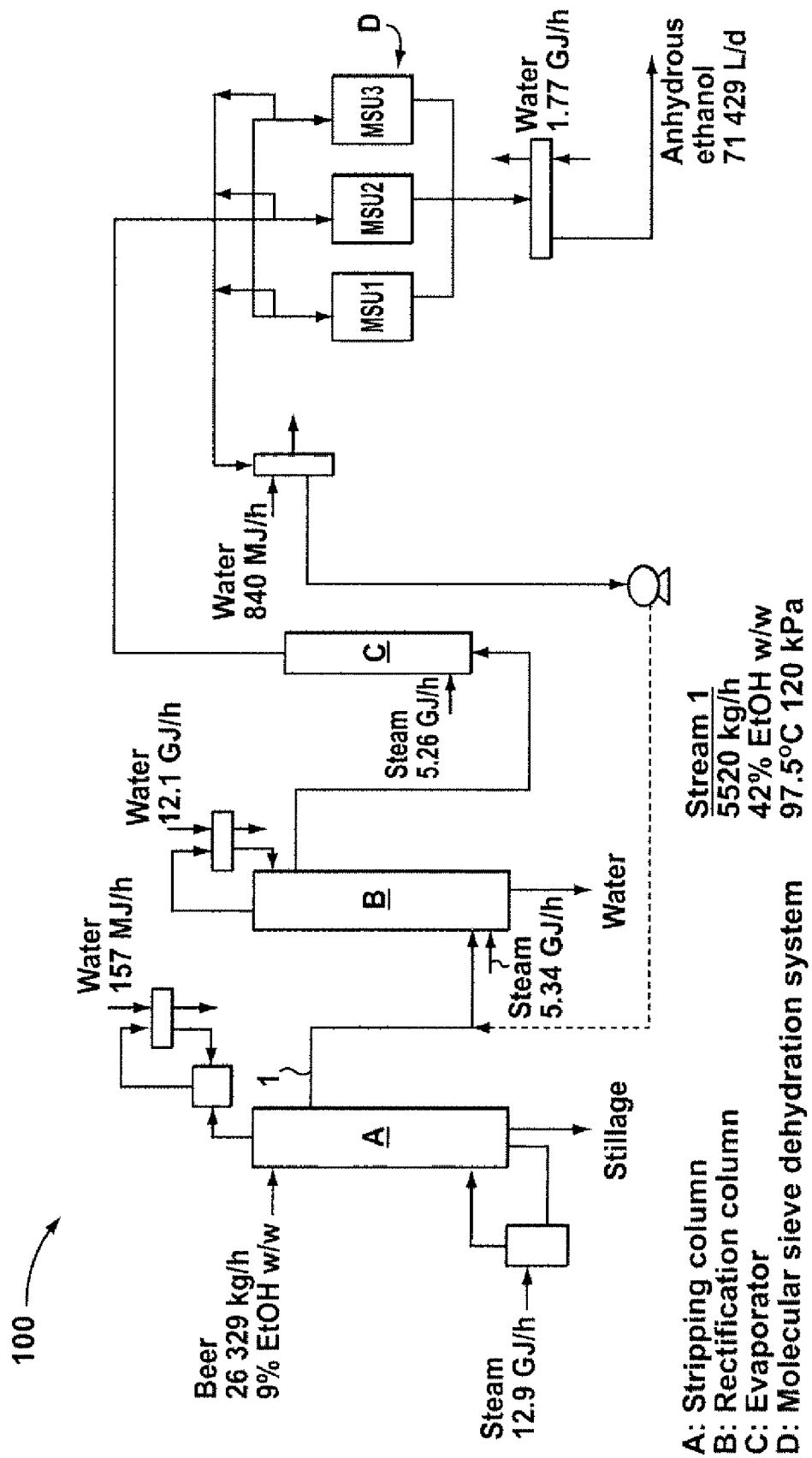
FIG. 7 is a flow sheet of the distillation and dehydration section of an ethanol plant using molecular sieves provided as the background for a comparative example.

Two examples of design applications, shown in FIGS. 8 and 9, using a membrane unit 38 in the ethanol industry and exhibiting benefits in reducing the process energy demand or increasing production compared to a process using molecular sieves without a membrane separation unit, shown in FIG. 7, are described hereinafter.

FIG. 7 shows a conventional process flow diagram of the distillation and dehydration sections 100 of a fuel ethanol plant, for example a fuel ethanol plant with an upstream fermentor fed for example with sugarcane, producing 71 429 L/day of anhydrous ethanol at 99.5% EtOH w/w (by weight). The primary pieces of equipment in the distillation and dehydration sections 100 of the plant are a stripping column A, a rectification column B, an evaporator C, and a pressure swing molecular sieve semi-continuous dehydration system D comprising three molecular sieve units, MSU1, MS2U, MSU3. Stripping column A and rectification column B are parts of a two-column distillation unit.

From a fermenter, beer at 9% EtOH w/w is fed at a rate of 26 329 kg/h into the stripping column A, from which a stream at 42% EtOH w/w is extracted and directed into the rectification column B. Stillage from the stripping column A comprises 0.02% EtOH w/w typically. A condensed stream from the rectification column B at 93% EtOH w/w is evaporated and pre-heated in the evaporator C prior to being fed into the molecular sieve system D, from which dehydrated ethanol vapour is recovered and condensed afterwards as a 99.5% EtOH w/w product.

The typical energy loads for the various components, as shown in FIG. 7, is 12.9 GJ/h required for steam for the stripping column A, 5.34 GJ/h required for steam for the rectification column B, and 5.26 GJ/h required for steam for the evaporator.

Figure 8:
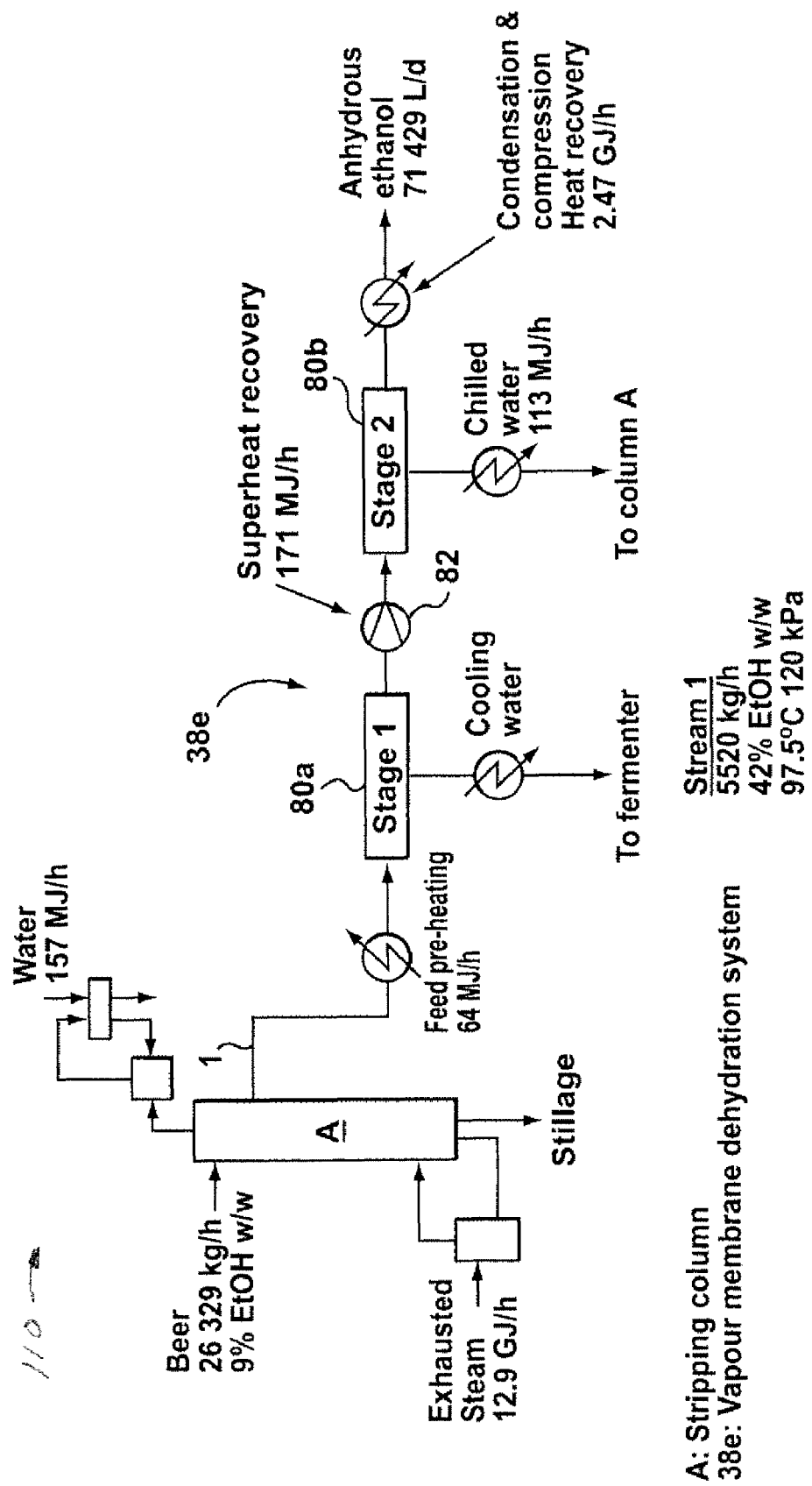
FIG. 8 is a flow sheet of the distillation and dehydration section of an ethanol plant using vapour separation membranes rather than the molecular sieves of FIG. 7.

An alternate distillation and dehydration section 110 using a membrane unit 38e to replace the rectification column B, the evaporator C and the molecular sieve dehydration system D of FIG. 7 is shown in FIG. 8. The alternate distillation and dehydration section 110 of FIG. 8 reduces the energy demand of the distillation and dehydration operations compared to the distillation and dehydration section 100 of FIG. 7.

The membrane unit 38e replaces the rectification column B, the evaporator C and the molecular sieve dehydration system D of FIG. 7, such that the distillation and dehydration section 110 of the ethanol plant now comprised two main processes and equipment units, the stripping column A and the membrane unit 38e.

The membrane unit 38e comprises two membrane stages 80a, 80b in series, with a compressor 82 between, which raises the pressure of the retentate issued from the first stage 80a from about 110 kPa to about 225 kPa. The permeate from both stages 80a, 80b is condensed. Permeate from the first stage 80a, at 0.1% EtOH w/w, is directed to a fermentation section of the plant, and permeate from the second stage 80b at 1.7% EtOH w/w is directed back for re-distillation to the stripping column A.

Using the membrane system 38e to replace the units B, C and D of the distillation and dehydration section 100 of FIG. 7 corresponds to a total savings of 5.34+5.26=10.60 GJ/h in steam energy. In addition, there is the potential to recover energy from the superheated compressed retentate from the first stage 80a, 171 MJ/h, and the latent heat of condensation of the retentate, dehydrated ethanol, issued from the second stage 80b, 2.47 GJ/h. However, there is 64 MJ/h demand for steam to pre-heat the feed stream from the stripping column A to the membrane unit 38e which is subtracted from the energy savings of the distillation and dehydration section 110 of FIG. 8. A total net energy savings, in the form of reduced energy required to generate steam, of 13.2 GJ/h results from using one distillation column (stripping column A) with further dehydration by the membrane unit 38e over a conventional coupling of a two column distillation unit (stripping column A and rectification column B) with further dehydration using an evaporator C and molecular sieve dehydrators D.

Figure 9:
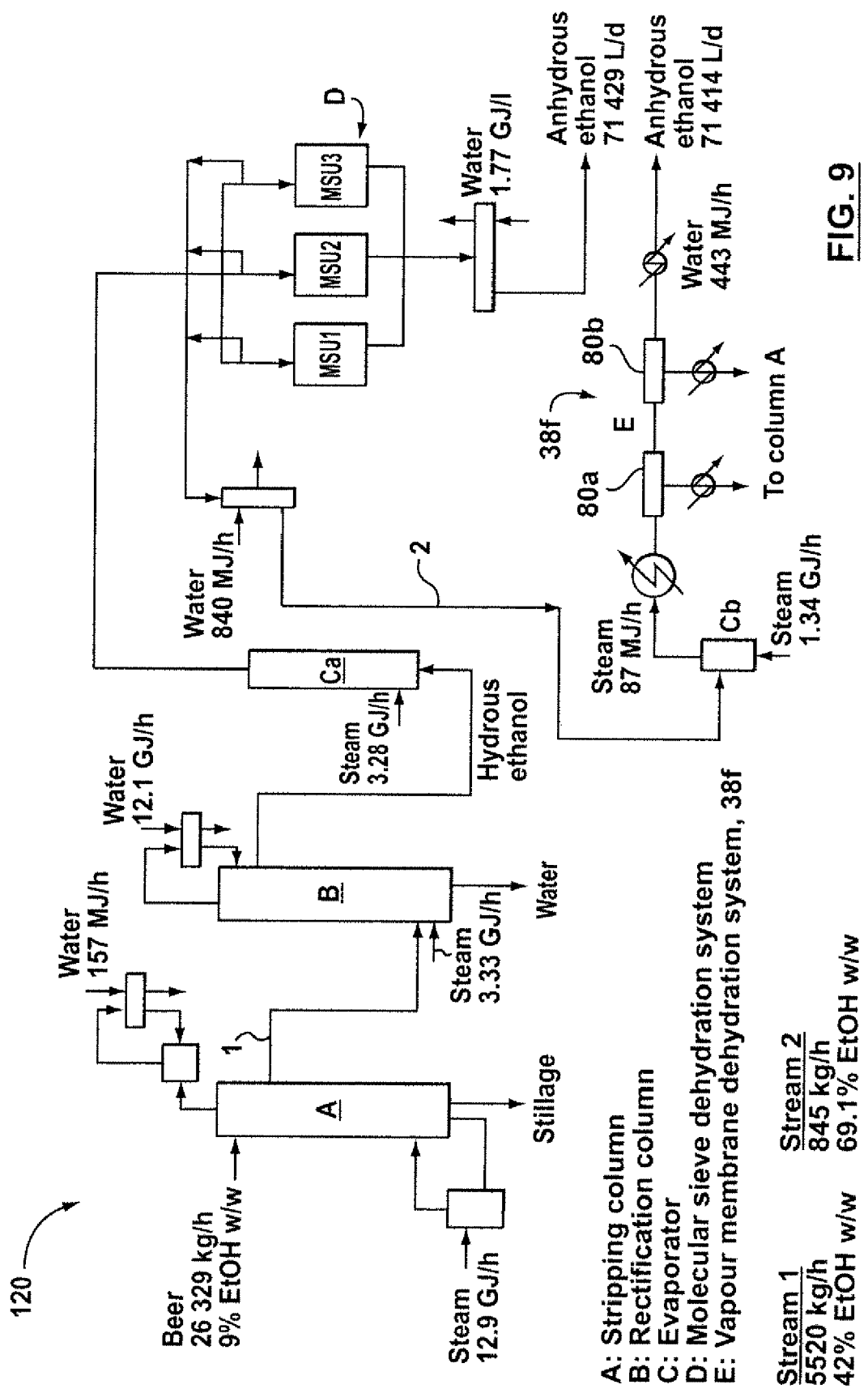
FIG. 9 is a flow sheet of the distillation and dehydration section of an ethanol plant using vapour separation membranes in combination with molecular sieves.

FIG. 9 illustrates another example of a design application of a membrane vapour separation process in a distillation and dehydration section 120 of an ethanol plant. The design results in energy savings and an increase in the dehydrated ethanol product yield compared to FIG. 7.

In this example, a rich-ethanol purge at 69.1% EtOH w/w issued from the molecular sieve system D is directed to a membrane unit 38f comprising two membrane stages 80a, 80b arranged in series. After evaporation, in a second evaporator Cb, and pre-heating, the rich-ethanol purge at 105° C. and a pressure of 162 kPa, is fed into the membrane unit 38f. The pressure of the retentate stream from the first stage 80a is reduced to 157.6 kPa and so there is no compression required on this stream ahead of the second membrane stage 80b. In the permeate line from the first stage 80a, the vacuum is set at 10 kPa absolute. In the permeate line from the second stage 80b, the vacuum is set at 2.5 kPa absolute. After condensation, the permeate from the first stage, at 1.2% EtOH w/w, and the permeate from the second stage, at 17.5% EtOH w/w, are routed back for re-distillation to the stripping column A. The total mass flow from both of these permeate streams corresponds to about 0.1% w/w of the flow of beer into the stripping column A. The flow rate of anhydrous ethanol product from the membrane unit 38f is 17 714 L/day, an increase in production by 24.8% compared to the conventional distillation and dehydration section 100 of FIG. 7.

Dehydrating the ethanol-rich purge, at 845 kg/h and 69.1% EtOH w/w, into the membrane 38f results in a significant reduction of the total mass flow that is distilled in the rectification column B and afterwards evaporated in the evaporator C. Consequently, the steam heat loads for units B and C are now reduced to the following values: 3.33 GJ/h steam for the rectification column B and 3.28 GJ/h steam for the evaporator C. With respect to the data presented for the conventional distillation and dehydration section 100 of FIG. 7, the total steam heat load for units B and C in FIG. 9 is reduced by 4.0 GJ/h.

With the membrane unit 38f, the electrical energy required for the powered equipment, which is chiller load for condensing the permeate from the membrane unit 38f and condensing the additional anhydrous ethanol produced by the membrane unit 38f and circulation and vacuum pumps, totals 45 MJ/h. The steam energy loads associated with the membrane unit 38f are respectively 1.34 GJ/h and 87 MJ/h for evaporation and pre-heating the ethanol-rich purge from the molecular sieve system D, for a total of 1.43 GJ/h of energy required.

Using the membrane unit 38f to treat the molecular sieve purge reduces the energy required to heat steam by 2.56 GJ/h, and the overall energy required is reduced by 2.51 GJ/h, with the additional benefit of a 24.8% increase in anhydrous ethanol production.

While various examples of devices or processes have been described above, various other specific devices or processes may also be within the scope of the invention defined by the following claims.

We claim:

1. A process for removing water from a mixture comprising ethanol and water, the process comprising steps of
   a) distilling the mixture to produce distillate;
   b) feeding at least a portion of the distillate to a gas separation membrane;
   c) collecting permeate from the gas separation membrane;
   d) compressing at least some of the permeate and using heat carried by the permeate to assist in distilling the mixture; and
   e) removing water from at least some of the distillate before feeding at least some of the distillate to the gas separation membrane, the step of removing water from at least some of the distillate including a step of passing the distillate through a molecular sieve.

2. The process of claim 1 further comprising compressing permeate and recycling it to a fermenter.

3. the process of claim 1 further comprising collecting a product vapour from the membrane and passing it through a heat exchanger.

4. the process of claim 1 wherein the permeate is 2% ethanol by volume or less.

5. The process of claim 1 wherein the mixture is partially de-watered after distilling the mixture and before feeding the distillate to the gas separation membrane.

6. The process of claim 1 wherein distillate for feeding to the gas separation membranes is collected from a purge stream of the molecular sieve.

7. The process of claim 1 wherein the step of distilling the mixture is performed in a single distillation column to an ethanol content of at least about 45% by weight.

8. A process of removing water from a mixture comprising ethanol vapour and water vapour, the process comprising steps of feeding the mixture through two or more membrane vapour separation stages wherein permeate from one stage is compressed for use as a supply of heat to an upstream distillation unit, and passing the distillate from the distillation unit through a molecular sieve to remove water from at least some of the distillate before feeding the distillate to the two or more membrane vapor separation stages.

9. The process of claim 8 wherein permeate from another stage is condensed and used as a source of water.

10. The process from claim 8 wherein permeate from a downstream stage is compressed and added to permeate from an upstream stage.

11. The process of claim 8 wherein permeate from a first stage is fed to a second stage and permeate from the second stage is compressed for use as a supply of heat.

12. The process of claim 1, wherein step d) comprises compressing the permeate substantially adiabatically to increase the temperature of the permeate.

13. The process of claim 1, wherein step d) comprises compressing the permeate using a compressor having a compression ratio of less than about 1:40.

* * * * *